United States Patent [19]

Archibald et al.

[11] 3,992,544

[45] Nov. 16, 1976

[54] TETRAHYDRO-PYRROLO[3,2-C]PYRIDINE DERIVATIVES

[75] Inventors: John Leheup Archibald, Windsor; Kenneth Heatherington, Burnham, both of England

[73] Assignee: John Wyeth & Brother, Ltd., Maidenhead, England

[22] Filed: Apr. 15, 1975

[21] Appl. No.: 568,355

[30] Foreign Application Priority Data

Apr. 24, 1974 United Kingdom............... 17812/74

[52] U.S. Cl............................ 424/263; 260/293.61; 260/293.8; 260/295 F; 260/296 H
[51] Int. Cl.².................................... C07D 471/04
[58] Field of Search................. 260/296 H; 424/263

[56] References Cited

OTHER PUBLICATIONS

Herz et al., "J. Amer. Chem. Soc." vol. 77 (1955), pp. 6353–6355.

Primary Examiner—Henry R. Jiles
Assistant Examiner—R. W. Ramsuer

[57] ABSTRACT

Certain novel 4,5,6,7-tetrahydro-1H-pyrrolo[3,2-c]pyridine derivatives and their pharmacologically acceptable salts are described. These compounds provide potent and non-toxic compositions for the treatment of hypertension. Certain of the disclosed compounds also display activity as anti-tremor agents.

10 Claims, No Drawings

TETRAHYDRO-PYRROLO[3,2-C]PYRIDINE DERIVATIVES

This invention relates to novel heterocyclic compounds, to processes for preparing them and to pharmaceutical compositions containing them.

More particularly this invention relates to novel tetrahydro-pyrrolo[3,2-c]pyridines of formula:

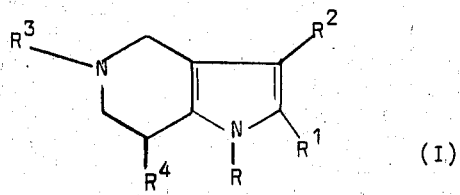

and the pharmaceutically acceptable acid addition and quaternary ammonium salts thereof, wherein R represents lower alkyl, aryl of 6 to 10 carbon atoms or aryl lower alkyl of 7 to 12 carbon atoms in either of which the aryl ring maybe substituted by halogen, lower alkyl or lower alkoxy; $R^1$ represents lower alkyl or aryl of 6 to 10 carbon atoms which may be substituted by halogen, lower alkyl or lower alkoxy; $R^2$ represents hydrogen, lower alkyl, —CHO,—CH=NOH, —$CH_2OCOR^5$, —$CH_2OR^6$ or —$CH_2NR^7R^8$ wherein $R^5$ represents lower alkyl, $R^6$ represents hydrogen or lower alkyl and $R^7$ and $R^8$ each represent lower alkyl or together with the nitrogen atom to which they are attached represent a pyrrolidino or piperidino radical; $R^3$ represents hydrogen, lower alkyl, benzoyl or aryl lower alkyl of 7 to 12 carbon atoms in which the aryl portion may be substituted by halogen, lower alkyl or lower alkoxy; and $R^4$ represents hydrogen or lower alkyl.

By the term lower alkyl as used herein is meant an alkyl group of 1 to 6 carbon atoms and includes both straight and branched chains.

The term aryl used alone or as part of another group including the aryl portion of an aroyl group covers carbocyclic rings possessing aromatic character.

Examples of lower alkyl radicals for the groups R, $R^1$, $R^2$, $R^3$, $R^4$, $R^5$, $R^6$, $R^7$ and $R^8$ are methyl, ethyl, n-propyl, isopropyl, n-butyl and isobutyl. The preferred lower alkyl group is methyl.

Examples of aryl radicals for the groups R and $R^1$ are phenyl and naphthyl both of which radicals may be substituted by one or more groups which may be the same or different; for example by halogen (for example fluorine, chlorine or bromine), lower alkyl (for example methyl, ethyl, propyl or butyl) or lower alkoxy (for example methoxy, ethoxy, propoxy or butoxy).

Examples of aryl lower alkyl radicals for the groups R and $R^3$ are benzyl, phenethyl, 3-phenylpropyl or 4-phenylbutyl all of which radicals may be substituted as above for the radical $R^1$ when phenyl.

Preferably R is phenyl or benzyl, either of which may be substituted by halogen, lower alkyl or lower alkoxy. Preferably $R^1$ is lower alkyl or phenyl. Preferably $R^2$ is hydrogen —CHO,—CH=NOH,—$CH_2OCOR^5$,$CH_2OH$-,—$CH_2O$-lower alkyl, —$CH_2N$(lower alkyl)$_2$. Preferably $R^3$ is hydrogen, lower alkyl or benzyl which may be mono substituted by halogen lower alkyl or lower alkoxy. $R^4$ is preferably lower alkyl.

Most preferably R is phenyl or benzyl either of which may be substituted as described above; $R^1$ is lower alkyl or phenyl; $R^2$ is hydrogen; $R^3$ is hydrogen, lower alkyl or benzyl which may be substituted by halogen, lower alkyl or lower alkoxy; and $R^4$ is methyl.

The acid addition salts of the compounds of formula (I) may be exemplified by salts formed with inorganic acids such as hydrochlorides, hydrobromides, sulphates, nitrates, phosphates; or salts formed with organic acids such as acetates, citrates, maleates, fumarates, formates and organic acid sulphonates, e.g. alkyl or aryl sulphonates.

Examples of quaternary ammonium salts are those formed with alkyl halides, e.g. methyl iodide, ethyl iodide or methyl bromide, and benzyl halides, e.g. benzyl bromide.

The novel compounds provided by the present invention possess hypotensive activity for example as demonstrated by a standard procedure and may also be intermediates for other compounds of the invention.

In addition, the novel compounds of this invention may also possess one or more of the following activities in standard pharmacological tests: anti-tremor activity, CNS depressant activity, and inhibition of blood platelet aggregation.

The compounds were tested for hypotensive activity by administering them orally to normotensive rats. For example representative compounds of formula I namely: 5-benzyl-4,5,6,7-tetrahydro-7-methyl-1,2-diphenyl-1-H-pyrrolo-[3,2-c]pyridine and 1-benzyl-4,5,6,7-tetrahydro-7-methyl-2-phenyl-1-H-pyrrolo[3,2-c]pyridine showed hypotensive activity at dose levels of 12.8 and 25.6 mpk.

The compounds were tested for anti-tremor activity by a method based on that by Everett et al., Science 124: 79, 1956. The procedure was to measure the effectiveness of the compound of formula I being tested to antagonise the effect of oxytremorine in mice. In such a test, 1,5-Dibenzyl 4,5,6,7-tetrahydro-2,7-dimethyl-1-H-pyrrolo[3,2-c]pyridine showed an $ED_{50}$ value in the range 16–30 mpk when administered orally. $ED_{50}$= effective dose for 50% of animals tested.

The following compounds of formula I also showed anti-tremor activity:
 1,5-Dibenzyl-4,5,6,7-tetrahydro-7-methyl-2-phenyl-1-H-pyrrolo[3,2-c]pyridino-3-carboxaldehyde;
 1,5-Dibenzyl-4,5,6,7-tetrahydro-3-methoxymethyl-7-methyl-1-H-pyrrolo[3,2-c]pyridine;
 1-Benzyl-4,5,6,7-tetrahydro-5,7-dimethyl-2-phenyl-1H-pyrrolo[3,2-c]pyridine.

In an in vitro test based on that by Born and Cross, J.Physiol., 168 pps 178–195(1963), 1-benzyl-4,5,6,7-tetrahydro-5,7-dimethyl-2-phenyl-1-H-pyrrolo[3,2-c]pyridine, showed moderate activity at a concentration of $0.13 \times 10^{-3}M$ as an inhibitor of blood platelet aggregation. Compounds possessing the ability to inhibit blood platelet aggregation are of value in the treatment of vascular disease, particularly in the treatment or prevention of vascular thrombosis in mammals.

It will be apparent to anyone skilled in the art that compounds of formula (I) may possess one or more asymmetric centres and therefore, optical isomers are possible. It is to be understood that all such optical isomers or mixtures thereof are intended to be within the scope of this invention.

The present invention further provides processes for preparing the compounds of formula (I). One such process for preparing compounds of formula I wherein $R^2$ is hydrogen or lower alkyl comprises reacting a compound of formula:

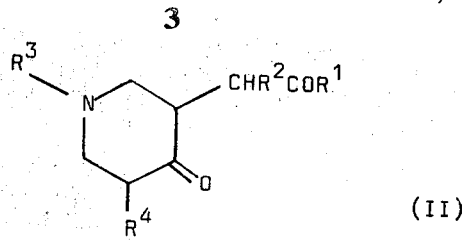

(II)

wherein $R^1$, $R^2$, $R^3$ and $R^4$ are as defined above; or an acid addition or quaternary ammonium salt thereof; with a primary amine of formula:

R-NH$_2$            (III)

wherein R is as defined above; or an acid addition salt thereof. Once a compound of formula I wherein $R^2$ is hydrogen is prepared then that compound may be converted by any one of the following processes, to give a corresponding compound of formula (I) wherein $R^2$ is a. a —CHO radical by formylation, which compound may be further reacted with hydroxylamine to give the corresponding oxime derivative wherein $R^2$ is —CH=NOH;

b. a —CH$_2$NR$^7$R$^8$ radical, wherein $R^7$ and $R^8$ are as hereinbefore defined, by reaction with formaldehyde and a compound of formula

R$^7$R$^8$NH            (IV)

wherein $R^7$ and $R^8$ are as hereinbefore defined, under Mannich reaction conditions;

c. a —CH$_2$OCOR$^5$ radical wherein $R^5$ is lower alkyl by reaction with formaldehyde and an acid of formula:

R$^5$COOH            (V)

wherein $R^5$ is as hereinbefore defined; which compound may be further reacted with a compound of formula (VI):

R$^6$-OH            (VI)

wherein $R^6$ is as defined above to give a corresponding compound of formula (I) wherein $R^2$ is a —CH$_2$OR$^6$ radical as defined above; and further, if desired, converting any of the compounds of formula (I) formed to their acid addition or quaternary ammonium salts.

The above reaction of compounds of formula (II) with compounds of formula (III) to give compounds of this invention may be conveniently carried out under Paal-Knorr reaction conditions for the preparation of pyrroles. For example, the reaction may be carried out in the presence of a solvent, e.g. a high boiling hydrocarbon, for example toluene, and in the presence of an acid, e.g. an organic acid, e.g. p-toluene sulphonic acid, or acetic acid. In connection with methods for effecting this reaction reference may also be made to the literature, for example to N. P. Buu-Hoï et al., J.Org.Chem., 20, 639 (1955) and S. G. P. Plant, J.Chem. Soc., 1595 (1930).

The present invention also includes any of the separate reaction processes (a), (b) or (c) above where a compound of formula (I), wherein R, $R^1$, $R^3$ and $R^4$ are as defined above and $R^2$ is hydrogen, is reacted to give a corresponding compound of formula (I) wherein $R^2$ is as defined above in connection with processes (a), (b) or (c).

The formylation process (a) may be conveniently carried out by using the Vilsmeier-Haack reaction procedure. For example the compound to be formylated may be reacted with a dialkyl or an alkyl aryl formamide in the presence of phosphorus oxychloride or phosgene. Reference may be made to the literature, including standard textbooks, concerning this reaction. Once a formylated derivative of the compound has been prepared it may be converted to the corresponding —CH=NOH derivative by standard reaction procedures using hydroxylamine.

In connection with process (b) above reference may be made to the literature for the standard methods of performing the Mannich reaction. For example the reaction may be effected by allowing the compound of formula (I) wherein $R^2$ is hydrogen to stand in the presence of formaldehyde and the amine of formula (IV) as defined above, preferably as the acid addition salt, e.g. the hydrochloride salt.

Reaction (c) above may be effected by allowing the compound of formula (I) wherein $R^2$ is hydrogen to stand in the presence of the acid of formula (V) as defined above, and formaldehyde for sufficient time to enable the reaction to occur. Once a compound of formula (I) wherein $R^2$ is —CH$_2$OCOR$^5$ wherein $R^5$ is as hereinbefore defined has been prepared then that compound may be converted to the corresponding compound of formula (I) wherein $R^2$ is —CH$_2$OR$^6$, as defined above, by reaction, preferably with heating, with a compound of formula (VI) as hereinbefore defined.

Compounds of formula (II) as hereinbefore defined, used as starting materials in the first-mentioned process above, may be prepared by reacting a compound of formula:

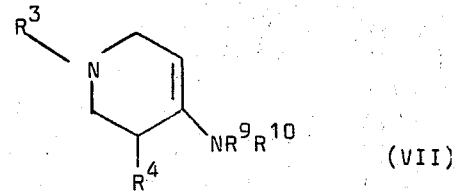

(VII)

wherein $R^3$ and $R^4$ are as defined above, $R^9$ and $R^{10}$ are lower alkyl radicals or $R^9$ and $R^{10}$ together with the nitrogen to which they are attached form a saturated heterocyclic ring, e.g. pyrrolidino; with a compound of formula:

R$^1$—CO—CHR$^2$—hal            (VIII)

wherein $R^1$ is as defined above, $R^2$ represents hydrogen or lower alkyl, and hal represents a halogen atom, e.g. chlorine or bromine. This reaction may be conveniently carried out in an inert solvent preferably under an inert atmosphere, e.g. nitrogen.

An alternative process for preparing compounds of formula (II) wherein $R^1$ is lower alkyl, other than a tertiary alkyl, comprises hydrating a compound of formula:

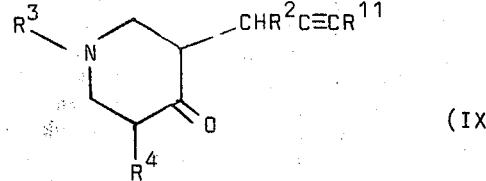

(IX)

wherein $R^3$ and $R^4$ are as hereinbefore defined, $R^2$ represents hydrogen or lower alkyl and $R^{11}$ represents an alkyl group of 1 to 5 carbon atoms. The hydration reaction may be effected by using a catalytic amount of a mercuric salt in the presence of aqueous sulphuric acid.

Compounds of formula (IX) may themselves be prepared from compounds of formula (VII) by reaction with an appropriately substituted acetylenic compound of formula:

$$R^{11}C \equiv C-CHR^2-hal \qquad (X)$$

wherein $R^2$ and $R^{11}$ are as defined in connection with formula (IX) and hal represents a halogen, e.g. chlorine or bromine.

Some of the compounds of formula (VII) are known compounds and reference may be made to the literature for methods for preparing them. Novel compounds of formula (VII) may be prepared by analogous processes.

When a compound of formula (I) is prepared in which $R^3$ is benzyl then this compound may be hydrogenolysed to give a corresponding compound of formula (I) wherein $R^3$ is hydrogen. Also when a compound of formula (I) is in the form of a quaternary ammonium salt of formula:

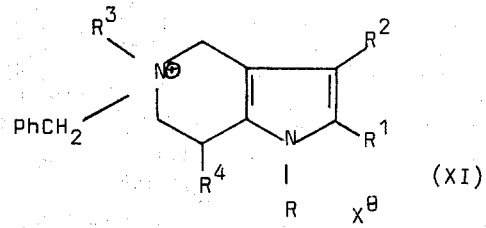

wherein R, $R^1$, $R^2$ and $R^4$ are as hereinbefore defined, $R^3$ is other than benzyl and $X^-$ is an anion then that compound may be hydrogenolysed to remove the benzyl group.

Removal of the benzyl group in the two reactions above may be effected using hydrogen and a palladium on charcoal catalyst.

When a compound of formula (I) is prepared in which $R^3$ is hydrogen then that compound may be converted by methods known in the art to corresponding compounds of formula (I) wherein $R^3$ is a lower alkyl, aroyl or aryl lower alkyl radical. For example, a compound of formula (I) wherein $R^3$ is lower alkyl or aryl lower alkyl may be prepared by alkylating the compound of formula (I) wherein $R^3$ is hydrogen with a compound of formula:

$$R^3 - Y \qquad (XII)$$

wherein $R^3$ is lower alkyl or aryl lower alkyl and Y is a halogen, e.g. chlorine or bromine, or an equivalent replaceable atom or group, e.g. a hydroxyl group or an organic sulphonyl radical such as a tosyl radical. When Y is a hydroxyl group the alkylation is preferably carried out in the presence of a catalyst, for example Raney Nickel. An organic solvent, which is inert under the reaction conditions, is usually used, for example xylene, toluene or benzene. Preferably the reaction is carried out by heating the reactants under reflux in a water-immiscible organic solvent, for example xylene, and removing the water formed during the reaction by azeotropic distillation. Similarly, compounds of formula (I) wherein $R^3$ is aroyl may be prepared by acylating a corresponding compound of formula (I) wherein $R^3$ is hydrogen.

The novel compounds provided by this invention may contain at least one basic nitrogen atom and thus can form acid addition salts with acids (particularly pharmaceutically acceptable acids) or quaternary ammonium salts, for example with alkyl halides or aralkyl halides (particularly methyl iodide or benzyl chloride or bromide). The acid addition salts may either be formed in situ during the hereinbefore described processes and isolated therefrom or a free base may be treated with the appropriate acid in the presence of a suitable solvent and then the salt isolated. The quaternary salts may be prepared by treating the free base with the appropriate halide in the presence or absence of a solvent.

This invention also provides a pharmaceutical composition comprising a compound of formula (I) as hereinbefore defined, together with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The following Examples illustrate the invention; Examples 1, 2, 5 and 6 concern the prepararion of starting materials; the remaining Examples concern the preparation of compounds of this invention: Starting materials for Examples 22 to 24, and 29 to 32 may be prepared by processes analogous to Examples 1 and 2, or 5 and 6, where applicable, using appropriate reactants.

EXAMPLE 1

1-Benzyl-1,2,3,6-tetrahydro-3-methyl-4-pyrrolidinopyridine

A mixture of 1-benzyl-3-methyl-4-piperidone (91 g), pyrrolidine (35.6 g), p-toluenesulphonic acid (0.5 g) and dry benzene (400 ml) was heated under reflux under a Dean and Stark trap until separation of water was complete. The solvent was removed on a rotary evaporator and the residue distilled to give 95 g of a colourless liquid boiling at 144°–6° C (0.01 mm).

EXAMPLE 2

1-Benzyl-3-methyl-5-phenacyl-4-piperidone

To a stirred, cooled solution of 1-benzyl-1,2,3,6-tetrahydro-3-methyl-4-pyrrolidinopyridine (14 g) in dry benzene (50 ml) was added dropwise, in an atmosphere of nitrogen, a solution of phenacyl bromide (10 g) in dry benzene (50 ml). The resulting solution was stirred at room temperature, under nitrogen for 40 hours. Water (100 ml) was added and stirring continued for 1 hour. The organic layer was collected, dried over magnesium sulphate and evaporated to give 17.3 g of the crude product as a red oil.

EXAMPLE 3

1,5-Dibenzyl-4,5,6,7-tetrahydro-7-methyl-2-phenyl-1H-pyrrolo[3,2-c]pyridine

A mixture of 1-benzyl-3-methyl-5-phenacyl-4-piperidone (3.2 g), benzylamine (1.1 g), p-toluenesulphonic acid (0.1 g) and dry toluene (100 ml) was heated under reflux under a Dean and Stark trap for 3 days. Removal of the solvent left a yellow solid, which on recrystallisation from methanol gave 3.3 g of the product as pale yellow prisms. M.pt. 131° C (Found: C 85.2; H, 7.2; N, 7.1. $C_{28}H_{28}N_2$ requires: C, 85.7; H, 7.2; N, 7.1%).

EXAMPLE 4

5-Benzyl-4,5,6,7-tetrahydro-7-methyl-1,2-diphenyl-1H-pyrrolo[3,2-c]pyridine

Following the procedure of Example 3 but substituting aniline for benzylamine the title compound was prepared. M.pt 138° C (Found: C, 85.9; H, 6.9; N, 7.1. $C_{27}H_{26}N_2$ requires: C, 85.7; H, 6.9; N, 7.4%)

EXAMPLE 5

1-Benzyl-3-methyl-5-prop-2-ynyl-4-piperidone

A solution of 1-benzyl-1,2,3,6-tetrahydro-3-methyl-4-pyrolidino-pyridine (14 g) and propargyl bromide (6 g) in dry benzene (50 ml) was stirred at room temperature under nitrogen for 40 hours. The mixture was then heated on a steam bath for one-half hour with water (200 ml). The organic layer was collected, dried over magnesium sulphate and evaporated, leaving 11.6 g of the crude title compound (about 50% by g.l.c.) as a red oil.

EXAMPLE 6

3-Acetonyl-1-benzyl-5-methyl-4-piperidone

A solution of the crude 1-benzyl-3-methyl-5-prop-2-ynyl-4-piperidone (10 g) from Example 5 in methanol (15 ml) was added dropwise to a stirred mixture of red mercuric oxide (1.5 g), boron trifluoride diethyletherate (1.1 ml), trichloroacetic acid (10 mg) and methanol (5 ml). The resulting mixture was stirred for 3 hours at room temperature and then filtered and the filtrate evaporated. The residue was treated at 50° C for 1 hour with 10% sulphuric acid (100 ml), the mixture filtered and the filtrate basified with sodium carbonate. Extraction with ether, drying of the extract with magnesium sulphate and evaporation gave 10.1 g of the crude title compound (about 75% by g.l.c.) as a brown oil.

EXAMPLE 7

1,5-Dibenzyl-4,5,6,7-tetrahydro-2,7-dimethyl-1H-pyrrolo[3,2-c]pyridine

Following the procedure of Example 3, but substituting 3-acetonyl-1-benzyl-5-methyl-4-piperidone for 1-benzyl-3-methyl-5-phenacyl-4-piperidone, the title compound was prepared M.pt. 99°–100° C (Found: C, 83.6; H, 8.0; N, 8.5. $C_{23}H_{26}N_2$ requires: C 83.6; H. 7.9; N, 8.5%).

EXAMPLE 8

1-Benzyl-4,5,6,7-tetrahydro-7-methyl-2-phenyl-1H-pyrrolo[3,2-c]pyridine

A solution of 1,5-dibenzyl-4,5,6,7-tetrahydro-7-methyl-2-phenyl-1H-pyrrolo[3,2-c]pyridine (5 g) and concentrated hydrochloric acid (2 ml) in 95% ethanol (250 ml) was hydrogenated at 55° C and 50 p.s.i. for 4 hours with 10% palladium on charcoal (2 g) as a catalyst. Removal of the catalyst and evaporation of the solvent gave an oil, which on treatment with aqueous ethanol gave 3.8 g of the hydrated hydrochloride of the title compound. M.pt. 214°–5° C (Found: C, 70.9; H, 7.0; N, 7.8. $C_{21}H_{23}ClN_2H_2O$ requires: C, 70.7; H, 7.1; N, 7.8%).

EXAMPLE 9

1,5-Dibenzyl-4,5,6,7-tetrahydro-5,7-dimethyl-2-phenyl-1H-pyrrolo[3,2-c]pyridinium iodide A mixture of 1,5-dibenzyl-4,5,6,7-tetrahydro-7-methyl-2-phenyl-1H-pyrrolo[3,2-c]pyridine (1 g), methyl iodide (2 ml) and absolute ethanol (100 ml) was kept at room temperature for 3 days. Removal of the solvent gave an oil which, on trituration with acetone, crystallised to give 1.22 g of the title compound. M.pt. 215° C (Found: C, 65.0; H, 6.0; N, 5.5. $C_{29}H_{31}IN_2$ requires: C, 65.2; H, 5.9; N, 5.2%).

EXAMPLE 10

1-Benzyl-4,5,6,7-tetrahydro-5,7-dimethyl-2-phenyl-1H-pyrrolo[3,2-c]pyridine

A solution of 1,5-dibenzyl-4,5,6,7-tetrahydro-5,7-dimethyl-2-phenyl-1H-pyrrolo[3,2-c]pyridinium iodide (1 g) in absolute ethanol (100 ml) was hydrogenated at 40° C and 50 p.s.i. for 18 hours with 10% palladium on charcoal (0.2 g) as a catalyst. Removal of the catalyst and evaporation of the solvent gave an oil, which was treated with 2N sodium hydroxide and extracted into ethyl acetate. The dried extract was evaporated to give an oil which crystallised on trituration with methanol to give 0.50 g of the title compound. M.pt. 90°–1° C. (Found: C, 83.2; H, 7.8; N, 9.1. $C_{22}H_{24}N_2$ requires: C, 83.5; H, 7.7; N, 8.9%).

EXAMPLE 11

1-Benzyl-4,5,6,7-tetrahydro-5,5,7-trimethyl-2-phenyl-1H-pyrrolo[3,2-c]pyridinium iodide 1-Benzyl-4,5,6,7-tetrahydro-7-methyl-2-phenyl-1H-pyrrolo[3,2-c]pyridine hydrochloride (0.9 g) was treated with triethylamine (0.5 g) and methyl iodide (0.35 g) in 50 ml of dimethylformamide and the mixture stirred for 3 days at room temperature. The solvent was removed by evaporation and the semi-solid residue shaken with 2N NaOH and ethyl acetate. Some solid remained undissolved which on recrystallisation from methanol gave the title compound as colourless needles (0.33 g) M.pt. 232°–3° C (Found: C, 60.0; H, 6.0; N, 6.0. $C_{23}H_{27}IN_2$ requires: C, 60.3; H, 5.9; N, 6.1%.)

EXAMPLE 12

1-Benzyl-4,5,6,7-tetrahydro-5,7-dimethyl-2-phenyl-1H-pyrrolo[3,2-c]pyridine

Fractional crystallisation of the ethyl acetate mother liquor obtained from the previous Example gave the title compound M.pt 88°–90° C.

EXAMPLE 13

1,5-Dibenzyl-4,5,6,7-tetrahydro-7-methyl-2-phenyl-1H-pyrrolo[3,2-c]pyridine-3-carboxaldehyde Phosphoryl chloride (1.68 g) was added dropwise to cooled dimethyl-formamide (1.60 g). A suspension of 1,5-dibenzyl-4,5,6,7-tetrahydro-7-methyl-2-phenyl-1H-pyrrolo[3,2-c]pyridine (3.92 g) in dimethylformamide (20 ml) was added portionwise. The resulting red solution was heated at 50° C for 4 hours, allowed to cool and poured on to 250 g ice. The mixture was basified with 2N sodium hydroxide, warmed gently for a few minutes, and the solid product collected by filtration, washed with water and dried. Two recrystallisations from methanol gave 2.86 g of the title compound as white needles. M.pt. 120°–1°. (Found: C, 83.2; H, 6.9; N, 6.5. $C_{29}H_{28}N_2O$ requires: C, 82.8; H, 6.7; N, 6.7%).

EXAMPLE 14

1,5-Dibenzyl-4,5,6,7-tetrahydro-7-methyl-2-phenyl-1H-pyrrolo[3,2-c]pyridine-3-carboxaldehyde oxime A mixture of the compound from Example 13 (1.0 g) hydroxylamine hydrochloride (0.5 g) and anhydrous pyridine (50 ml) was stirred at room temperature for 18 hours and poured into 2N hydrochloric acid (500 ml). A gummy precipitate was formed, which was separated and crystallised by heating with methanol to give the oxime (0.9 g) M.pt 171°–2° C. (Found: C, 80.3; H, 6.9; N, 9.6. $C_{29}H_{29}N_3O$ requires: C, 80.0, H, 6.7; N, 9.6%).

EXAMPLE 15

1,5-Dibenzyl-4,5,6,7-tetrahydro-2,7-dimethyl-1H-pyrrolo[3,2-c]pyridine-3-carboxaldehyde Following the procedure of Example 13, 1,5-dibenzyl-4,5,6,7-tetrahydro-2,7-dimethyl-1H-pyrrolo[3,2-c]pyridine was formylated to produce the title compound M.pt 149°–151° C. (Found: C, 80.8; H, 7.5; N, 7.8. $C_{24}H_{26}N_2O$ requires: C, 80.4; H, 7.3; N, 7.8%).

EXAMPLE 16

3-Acetoxymethyl-1,5-dibenzyl-4,5,6,7-tetrahydro-7-methyl-2-phenyl-1H-pyrrolo[3,2-c]pyridine A mixture of 1,5-dibenzyl-4,5,6,7-tetrahydro-7-methyl-2-phenyl-1H-pyrrolo[3,2-c]pyridine (2 g), formaldehyde (1 ml 40% aqueous solution) and dimethylamine hydrochloride (1 g) in glacial acetic acid (20 ml) was kept at room temperature for 3 days and then poured into water (150 ml). The mixture was extracted with ether (2 × 100 ml), the ether extracts washed with saturated sodium carbonate solution (3 × 100 ml), dried over magnesium sulphate and evaporated. Trituration of the resulting oil with ether gave the title compound as white needles. 0.82 g M.pt. 126° C (Found: C, 79.8; H, 7.1; N, 6.0. $C_{31}H_{30}N_2O_2$ requires: C, 80.1; H, 6.9; N, 6.0.

EXAMPLE 17

1,5-Dibenzyl-3-dimethylaminomethyl-4,5,6,7-tetrahydro-7-methyl-2-phenyl-1H-pyrrolo[3,2-c]pyridine Extraction of the aqueous residue from Example 16 with chloroform and work-up as in Example 16 gave the title compound as a brown oil (0.9 g).

EXAMPLE 18

3-Acetoxymethyl-1,5-dibenzyl-4,5,6,7-tetrahydro-7-methyl-2-phenyl-1H-pyrrolo[3,2-c]pyridine The title compound was prepared in 80% yield by following the procedure described in Example 16, but omitting the dimethylamine hydrochloride.

EXAMPLE 19

1,5-Dibenzyl-4,5,6,7-tetrahydro-3-methoxymethyl-7-methyl-2-phenyl-1H-pyrrolo[3,2-c]pyridine 3-Acetoxymethyl-1,5-dibenzyl-4,5,6,7-tetrahydro-7-methyl-2-phenyl-1H-pyrrolo[3,2-c]pyridine (200 mg), prepared according to Example 16, was dissolved in methanol (10 ml) by briefly warming. On cooling, the title compound was obtained as white needles, 125 mg. M.pt. 140°–1° C (Found: C, 82.5; H, 7.5; N, 6.4. $C_{30}H_{32}N_2O$ requires: C, 82.5; H, 7.4; N, 6.4%).

EXAMPLE 20

1,5-Dibenzyl-3-ethoxymethyl-4,5,6,7-tetrahydro-7-methyl-2-phenyl-1H-pyrrolo[3,2-c]pyridine Following the procedure of Example 19, but substituting ethanol for methanol, the title compound was obtained M.pt. 96°–8° C. (Found: C, 82.5; H, 7.8; N, 5.9%. $C_{31}H_{34}N_2O$ requires: C, 82.6; H, 7.6; N, 6.2%).

EXAMPLE 21

1,5-Dibenzyl-3-dimethylaminomethyl-4,5,6,7-tetrahydro-2,7-dimethyl-1H-pyrrolo[3,2-c]pyridine Following the procedure of Example 17, but using 1,5-dibenzyl-4,5,6,7-tetrahydro-2,7-dimethyl-1H-pyrrolo[3,2-c]pyridine as starting material, the title compound was obtained in 73% yield as a brown oil.

EXAMPLE 22

1-Benzyl-5-(p-chlorobenzyl)-4,5,6,7-tetrahydro-2,7-dimethyl-1H-pyrrolo[3,2-c]pyridine Following the procedure of Example 3 but substituting 3-acetonyl-1-(p-chlorobenzyl)-5-methyl-4-piperidone for 1-benzyl-3-methyl-5-phenacyl-4-piperidone the title compound may be be prepared.

EXAMPLE 23

1-Benzyl-5-(p-methylbenzyl)-4,5,6,7-tetrahydro-2,7-dimethyl-1H-pyrrolo[3,2-c]pyridine Following the procedure of Example 3 but substituting 3-acetonyl-1-(p-methylbenzyl)-5-methyl-4-piperidone for 1-benzyl-3-methyl-5-phenacyl-4-piperidone the title compound may be prepared.

EXAMPLE 24

1-Benzyl-5-(p-methoxybenzyl)-4,5,6,7-tetrahydro-2,7-dimethyl-1H-pyrrolo[3,2-c]pyridine Following the procedure of Example 3 but substituting 3-acetonyl-1-(p-methoxybenzyl)-5-methyl-4-piperidone for 1-benzyl-3-methyl-5-phenyl-4-piperidone the title compound may be prepared.

EXAMPLE 25

5-Benzyl-4,5,6,7-tetrahydro-1,2,7-trimethyl-1H-pyrrolo[3,2-c]pyridine

Using a procedure analogous to Example 3, 3-acetonyl-1-benzyl-5-methyl-4-piperidone may be reacted with methylamine to give the title compound.

EXAMPLE 26

5-Benzyl-1-(p-chlorobenzyl)-4,5,6,7-tetrahydro-2,7-dimethyl-1H-pyrrolo[3,2-c]pyridine Using a procedure analogous to Example 3, 3-acetonyl-1-benzyl-5-methyl-4-piperidone may be reacted with p-chlorobenzylamine to give the title compound.

EXAMPLE 27

5-Benzyl-1-(p-methylbenzyl)-4,5,6,7-tetrahydro-2,7-dimethyl-1H-pyrrolo[3,2-c]pyridine Using a procedure to analogous to Example 3, 3-acetonyl-1-benzyl-5-methyl-4-piperidone may be reacted with p-methylbenzylamine to give the title compound.

EXAMPLE 28

5-Benzyl-1-(p-methoxybenzyl)-4,5,6,7-tetrahydro-2,7-dimethyl-1H-pyrrolo[3,2-c]pyridine Using a procedure analogous to Example 3, 3-acetonyl-1-benzyl 5-methyl-4-piperidone may be reacted with p-methoxybenzylamine to give the title compound.

EXAMPLE 29

5-Benzyl-4,5,6,7-tetrahydro-7-methyl-1,2-di-(p-chlorophenyl)-1H-pyrrolo[3,2-c]pyridine Using a procedure analogous to Example 3, 1-benzyl-3-methyl-5-(p-chlorophenacyl)-4-piperidone may be reacted with p-chloroaniline to give the title compound.

EXAMPLE 30

1,5-Dibenzyl-4,5,6,7-tetrahydro-2,3,7-trimethyl-1H-pyrrolo[3,2-c]pyridine

Using a procedure analogous to Example 3, 1-benzyl-5-methyl-3-(1-methylacetonyl)-4-piperidone may be reacted with benzylamine to give the title compound.

EXAMPLE 31

1-benzyl-5-benzoyl-4,5,6,7-tetrahydro-2,7-dimethyl-1H-pyrrolo[3,2-c]pyridine

Using a procedure analogous to Example 3, 3-acetonyl-1-benzoyl-5-methyl-4-piperidone may be reacted with benzylamine to give the title compound.

EXAMPLE 32

1,5-Dibenzyl-4,5,6,7-tetrahydro-2-methyl-1H-pyrrolo[3,2-c]pyridine

Using a procedure analogous to Example 3, 3-acetonyl-1-benzyl-4-piperidone may be reacted with benzylamine to give the title compound.

EXAMPLE 33

1,5-Dibenzyl-3-hydroxymethyl-4,5,6,7-tetrahydro-7-methyl-2-phenyl-1H-pyrrolo[3,2-c]pyridine 3-Acetoxymethyl-1,5-dibenzyl-4,5,6,7-tetrahydro-7-methyl-2-phenyl-1H-pyrrolo[3,2-c]pyridine, prepared according to Example 18, may be hydrolysed to give the title compound.

EXAMPLE 34

1,5-Dibenzyl-3-piperidinomethyl-4,5,6,7-tetrahydro-2,7-dimethyl-1H-pyrrolo[3,2-c]pyridine Using a procedure analogous to Example 17, 1,5-dibenzyl-4,5,6,7-tetrahydro-2,7-dimethyl-1H-pyrrolo[3,2-c]pyridine may be reacted with piperidine hydrochloride and formaldehyde to give the title compound.

We claim:
1. A compound of the formula:

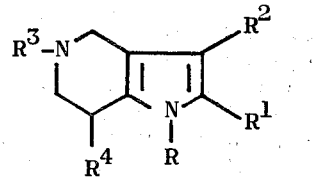

wherein R is lower alkyl, aryl lower alkyl of from 7 to 12 carbon atoms, phenyl, lower alkyl phenyl, halophenyl, lower alkoxyphenyl, naphthyl, halonaphthyl, lower alkoxy naphthyl, or lower alkyl naphthyl; $R^1$ is lower alkyl, phenyl, halophenyl, lower alkoxy phenyl, lower alkyl phenyl, naphthyl, halonaphthyl, lower alkyl naphthyl, or lower alkoxy naphthyl; $R^2$ is hydrogen, lower alkyl, —CHO, —CH=NOH, or —CH$_2$OR$^5$ wherein $R^5$ is hydrogen or lower alkyl; $R^3$ is hydrogen lower alkyl, benzoyl, aryl lower alkyl of from 7 to 12 carbon atoms or aryl lower alkyl of from 7 to 12 carbon atoms wherein the aryl portion is substituted by halogen, lower alkyl or lower alkoxy; $R^4$ is hydrogen or lower alkyl; or the pharmaceutically acceptable acid addition or quaternary ammonium salts thereof.

2. The compounds of claim 1 wherein $R^2$ is hydrogen or lower alkyl or the pharmaceutically acceptable acid addition or quaternary ammonium salts thereof.

3. A compound according to claim 1 which is 5-benzyl-4,5,6,7-tetrahydro-7-methyl-1,2-diphenyl-1H-pyrrolo[3,2-c]pyridine.

4. A compound according to claim 1 which is 1-benzyl-4,5,6,7-tetrahydro-7-methyl-2-phenyl-1H-pyrrolo[3,2-c]pyridine.

5. A compound according to claim 1 which is 1,5-Dibenzyl-4,5,6,7-tetrahydro-7-methyl-2-phenyl-1H-pyrrolo[3,2-c]pyridine-3-carboxaldehyde.

6. A compound according to claim 1 which is 1,5-Dibenzyl-4,5,6,7-tetrahydro-3-methoxymethyl-7-methyl-1H-pyrrolo[3,2-c]pyridine.

7. A compound according to claim 1 which is 1-Benzyl-4,5,6,7-tetrahydro-5,7-dimethyl-2-phenyl-1H-pyrrolo[3,2-c]pyridine.

8. A compound according to claim 1 which is 1,5-Dibenzyl-4,5,6,7-tetrahydro-2,7-dimethyl-1H-pyrrolo[3,2-c]pyridine.

9. A pharmaceutical composition suitable for administration to an animal suffering from hypertension comprising an anti-hypertensive amount of a compound of claim 1, and a pharmacologically acceptable carrier.

10. A pharmaceutical composition suitable for administration to an animal suffering from tremors, comprising an effective amount of a compound selected from the group consisting of:
  1. 1,5-Dibenzyl-4,5,6,7-tetrahydro-2,7-dimethyl-1H-pyrrolo[3,2-c]pyridine;
  2. 1,5-Dibenzyl-4,5,6,7-tetrahydro-7-methyl-2-phenyl-1H-pyrrolo[3,2-c]pyridino-3-carboxaldehyde;
  3. 1,5-Dibenzyl-4,5,6,7-tetrahydro-3-methoxymethyl-7-methyl-1H-pyrrolo[3,2-c]pyridine; and
  4. 1-Benzyl-4,5,6,7tetrahydro-5,7-dimethyl-2-phenyl-1H-pyrrolo[3,2-c]pyridine;
and a pharmacologically acceptable carrier.

* * * * *